US008546453B2

(12) United States Patent
Zhang

(10) Patent No.: US 8,546,453 B2
(45) Date of Patent: Oct. 1, 2013

(54) PROPOFOL COMPOSITIONS AND METHODS FOR REDUCING PAIN ASSOCIATED WITH PROPOFOL INJECTION

(76) Inventor: Rensheng Zhang, Gainesville, FL (US)

( * ) Notice: Subject to any disclaimer, the term of this patent is extended or adjusted under 35 U.S.C. 154(b) by 1842 days.

(21) Appl. No.: 10/918,248

(22) Filed: Aug. 13, 2004

(65) Prior Publication Data

US 2005/0049314 A1    Mar. 3, 2005

Related U.S. Application Data

(60) Provisional application No. 60/495,288, filed on Aug. 14, 2003.

(51) Int. Cl.
*A01N 31/08*    (2006.01)
(52) U.S. Cl.
USPC .......................................... 514/731; 424/450
(58) Field of Classification Search
None
See application file for complete search history.

(56) References Cited

U.S. PATENT DOCUMENTS

| | | | |
|---|---|---|---|
| 4,452,817 A | 6/1984 | Glen et al. | |
| 5,308,874 A | 5/1994 | Sanchez et al. | |
| 5,461,080 A | 10/1995 | Sanchez et al. | |
| 5,714,520 A | 2/1998 | Jones et al. | |
| 5,908,869 A | 6/1999 | Jones et al. | |
| 6,028,108 A | 2/2000 | George | |
| 6,100,302 A | 8/2000 | Pejaver et al. | |
| 6,140,374 A | 10/2000 | May et al. | |
| 6,147,122 A | 11/2000 | Mirejovsky et al. | |
| 6,177,477 B1 | 1/2001 | George et al. | |
| 6,254,853 B1* | 7/2001 | Hendler et al. | 424/45 |
| 6,326,406 B1 | 12/2001 | De Tommaso | |
| 6,399,087 B1 | 6/2002 | Zhang et al. | |
| 2003/0207946 A1* | 11/2003 | Park et al. | 514/731 |
| 2005/0020674 A1* | 1/2005 | Jenkins et al. | 514/488 |

FOREIGN PATENT DOCUMENTS
WO    WO 0197779 A2 * 12/2001

OTHER PUBLICATIONS

Kau, Yi-Cuan (2000). Propofol-sodium thiopental admixture reduces pain on injection. ACTA Anaesthesiology SIN 38:9-13.*
Aarts, L. et al. "The widely used anesthetic agent propofol can replace α-tocopherol as an antioxidant" *FEBS Let.*, 1995, 357(1):83-85.
Boer, F. et al. "Effect of propofol on peripheral vascular resistance during cardiopulmonary bypass" *Br. J. Anaesth.*, 1990, 65:184-189.
Borgeat, A. et al. "The nonhypnotic therapeutic applications of propofol" *Anesthesiology*, 1994, 80:642-656.
Castano, I. et al. "Infusion of propofol as anesthetic and antiemetic drug" *Rev. Esp. Anestesiol. Reanim.*, 1995, 42(7):257-260, abstract.
Cervantes, M. et al. "Effects of propofol on alterations of multineuronal activity of limbic and mesencephalic structures and neurological deficit elicited by acute global cerebral ischemia" *Arch. Med. Res.*, 1995, 26(4):385-395, abstract.
Crowther, J. et al. "Growth of microorganisms in propofol, thiopental, and a 1:1 mixture of propofol and thiopental" *Anesth. Analg.*, 1996, 82:475-478.
Diprivan, Injectable Emulsion Propofol, Professional Information Brochure, AstraZeneca, Apr. 2001.
Doenicke, A.W. et al. "Reducing pain during propofol injection: the role of the solvent" *Anesth. Analg.*, 1996, 82:472-474.
Eriksson, M. et al. "Effect of lignocaine and pH on propofol-induced pain" *Br. J. Anaesthesia*, 1997, 78(5):502-506.
Eriksson, O. et al. "Inhibition of lipid peroxidation in isolated rat liver mitochondria by the general anaesthetic propofol" *Biochem. Pharmacol.*, 1992, 44:391-393.
Ganta, R. and Fee, J.P.H. "Pain on injection of propofol: comparison of lignocaine with metoclopramide" *Br. J. Anaesthesia*, 1992, 69:316-317.
Klement, W. and Arndt, J.O. "Pain on I.V. injection of some anaesthetic agents is evoked by the unphysiological osmolality or pH of their formulations" *Br. J. Anaesth.*, 1991, 66:189-195.
Klement, W. and Arndt, J.O. "Pain on injection of propofol: effects of concentration and diluent" *Br. J. Anaesth.*, 1991, 67:281-284.
Kuisma, M. and Roine, R.O. "Propofol in prehospital treatment of convulsive status epilepticus" *Epilepsia*, 1995, 36(12):1241-1243.
Lazar, E.R. et al. "Propofol and thiopental in a 1:1 volume mixture is chemically stable" *Anesth. Analg.*, 1998, 86:422-426.
Lowson, S. et al. "Anticonvulsant properties of propofol and thiopentone: comparison using two tests in laboratory mice" *Brit. J. Anesthesia*, 1990, 64:59-63.
Macario, A. et al. "Which clinical anesthesia outcomes are both common and important to avoid? The perspective of a panel of expert anesthesiologists" *Anesth. Analg.*, 1999, 88:1085-1091.
McCulloh, M.J. and Lees, N.W. "Assessment and modification of pain on induction with propofol (Diprivan)" *Anaesthesia*, 1985, 40:1117-1120.
Murphy, P.G. et al. "The antioxidant potential of propofol (2,6-diisopropylphenol)" *Br. J. Anaesth.*, 1992, 68:613-618.
Musacchio, E. et al. "Antioxidant action of propofol on liver microsomes, mitochondria and brain synaptosomes in the rat" *Pharmacol. Toxicol.*, 1991, 69:75-77.
Nicol, M.E. et al. "Modification of pain on injection of propofol—a comparison between lignocaine and procaine" *Anaesthesia*, 1991, 46:67-69.
Picard, P. and Tramer, M.R. "Prevention of pain on injection with propofol: A quantitative systematic review" *Anesth. Analg.*, 2000, 90:963-969.
Propofol, Injectable Emulsion Propofol, Professional Information Brochure, Baxter Healthcare Corporation, Jul. 2002.

(Continued)

Primary Examiner — Lezah Roberts
Assistant Examiner — Nannette Holloman
(74) Attorney, Agent, or Firm — Saliwanchik, Lloyd & Eisenschenk

(57) ABSTRACT

The present invention pertains to pharmaceutical formulations containing propofol, methods for making such formulations, and methods for administering propofol at a pH above about 6.5, wherein the pain normally associated with propofol administration is reduced.

13 Claims, No Drawings

(56) References Cited

OTHER PUBLICATIONS

Robinson, B.J. et al. "Mechanisms whereby propofol mediates peripheral vasolidation in humans: sympathoinhibition or direct vascular relaxation" *Anesthesiology*, 1997, 86(1):64-72.

Rouby, J.J. et al. "Peripheral vascular effects of thiopental and propofol in humans with artificial hearts" *Anesthesiology*, 1991, 75:32-42.

Zhang, R.V. et al. "Propofol injection pain alleviated by thiopental—the role of the alkalotic buffering capacity" *Anesthesiology*, 2003, 99:A46, abstract No. A-46; available online Aug. 4, 2003; poster session presented at the Annual Meeting of the American Society of Anesthesiologists on Oct. 13, 2003.

\* cited by examiner

PROPOFOL COMPOSITIONS AND METHODS FOR REDUCING PAIN ASSOCIATED WITH PROPOFOL INJECTION

CROSS-REFERENCE TO RELATED APPLICATION

The present application claims the benefit of U.S. Provisional Application Ser. No. 60/495,288, filed Aug. 14, 2003, which is hereby incorporated by reference herein in its entirety, including any figures, tables, nucleic acid sequences, amino acid sequences, and drawings.

BACKGROUND OF THE INVENTION

Propofol (2,6-diisopropylphenol or 2,6-bis(1-methylethyl)-phenol)) is a widely used injectable, alkylphenol sedative-hypnotic agent widely used for induction and maintenance of general anesthesia or sedation. Intravenous injection of a therapeutic dose of propofol produces hypnosis rapidly with minimal excitation, usually within 40 seconds from the start of injection (the time for one arm-brain circulation). As with other rapidly acting intravenous anesthetic agents, the half-time of the blood-brain equilibrium is approximately 1 to 3 minutes, which accounts for the rapid induction of anesthesia. Thus, propofol has the advantage of a rapid onset after infusion or bolus injection, along with a short recovery period of several minutes, instead of hours. Since its introduction in the late 1980s, propofol's versatility and favorable pharmacokinetics have made it a popular choice for induction and maintenance of anesthesia.

Propofol has the disadvantage of causing pain upon injection. Among 33 clinical problems identified in the field of anesthesia, propofol-induced pain has been ranked seventh, when both clinical importance and frequency were considered (Macario A. et al., *Anesth. Analg.* 88:1085-1091, 1999). The mechanism by which propofol induces pain on injection is still not known. Various factors have been hypothesized to be responsible for this adverse effect, such as the osmality of the solvent used in the preparation, the pH of the preparation, or the concentration of propofol in the aqueous phase of the emulsion (Doenicke A. W. et al., *Anesth. Analg.* 82:472-474, 1996). One mechanism for the pain experienced after injection of propofol is thought to be the direct stimulation of venous nociceptive receptors or free nerve endings, the nerve impulse being transmitted by thinly myelinated A delta fibers (Arndt J. O. and Klement W., *Br. J. Anaesth.*, 66:189-195, 1991).

Many methods have been investigated to reduce the incidence and severity of propofol-induced pain, many of which involve the temperature of the formulation, size and site of venous cannulation, speed of injection, and analgesic interventions (Picard P. and Tramer M. R., *Anesth. Analg.* 90:963-969, 2000). Numerous pharmacological treatments, various doses and combinations, alternative methods of administration, and physical interventions have been tested, often with a clear physiological basis. Propofol has been warmed or cooled, injected faster or more slowly, with or without tourniquet, diluted or undiluted. Local anesthetics, opioids, non-steroidal anti-inflammatory drugs, ketamine, metoclopramide, droperidol, and other chemical substances have been evaluated.

Pain on injection induced by propofol has been found to be reduced by a preceding injection of lignocaine (also referred to as lidocaine) (McCulloh M. J. and Lees N. W., *Anaesthia,* 40:1117-1120, 1985). Low concentrations of lidocaine mixed with propofol (e.g., 1:10) and thereby diluted to a 0.1% solution almost instantaneously prevent propofol-induced pain on injection. Lidocaine's effects on vascular smooth muscle have been implicated (Nicol M. E. et al., *Anaesthesia,* 46:67-69, 1991). An effect of lidocaine on propofol-induced pain separate from its local anaesthetic action has also been proposed. Alternative explanations for the efficacy of lidocaine on injection pain caused by propofol include: lidocaine hydrochloride is a weak free base-cation solution which, when exposed to lipids, liberates protons as the free base dissolves in the lipids, thereby decreasing the pH of the mixture; the lower pH produced after mixing lidocaine with propofol reduces the concentration of propofol anions since propofol is a weak acid with a $pK_a$ of 11. This would result in an increased amount of propofol that migrates into the lipid phase, resulting in reduced pain on injection (Klement W. and Arndt J. O., *Br. J. Anaesth.,* 67:281-284, 1991; Babl J. et al., *Euro. J. Hospital Pharmacy,* 1:15-22, 1995).

It has also been proposed that local anaesthetics may bind to the vascular endothelium and that binding of the local anesthetic directly to propofol may also reduce its anesthetic effects. This would explain the observed reduction of propofol-induced pain on injection by metoclopramide, a structural analog of procainamide that is almost entirely lacking in local anaesthetic activity (Ganta R. and Fee. J. P. H., *Br. J. Anaesthesia,* 69:316-317, 1992). Like lignocaine, the pH-lowering effect of the metcolpramide solution has been suggested as the principal mechanism for its reported pain relieving effect, as well (Eriksson, M. et al., *Br. J. Anaesthesia,* 78:502-506, 1997).

Propofol is very lipid soluble and only slightly soluble in water and, thus, is formulated in an oil-in-water emulsion. The commercially available form of propofol, DIPRIVAN (for human use) and RAPINOVET (for veterinary use), is an opaque oil-in-water emulsion containing lipids and egg lecithin as an emulsifying agent (ASTRAZENECA, Wilmington, Del.). The DIPRIVAN 1% emulsion-type formulation contains 10 mg/mL propofol, 100 mg/mL soybean oil, 22.5 mg/mL glycerol, 12 mg/mL egg lecithin, and 0.005% w/v disodium edentate (EDTA), and is reported by the manufacturer to have a pH of 7.0 to 8.5 at time of packaging (DIPRIVAN, Injectable Emulsion Propofol, Professional Information Brochure, ASTRAZENECA, April 2001). Although the manufacturer's professional information brochure indicates that the propofol formulation also contains sodium hydroxide, there is no indication that any agent is added to the formulation to specifically maintain the alkalotic pH. The present inventor has determined that the pH of commercially available propofol formulations is significantly lower at the time the formulation is to be administered than that represented in the literature. This difference in pH may be explained by at least one of two phenomenon: (1) inaccurate measurement at time of manufacture/packaging (e.g., due to calibration drift or variations in moisture or temperature); and (2) the propofol formulation "drifts" such that, at the time of administration, the pH is significantly reduced, typically 5.8 to 6.0, or less. In contrast, according to the information brochure (July 2002) provided with a generic form of propofol that is commercially available from BAXTER Healthcare Corporation (Deerfield, Ill.; U.S. Pat. No. 6,147,122), the 1% propofol injectable emulsion has a pH of 4.5 to 6.6 at time of packaging. Injection pain is experienced with both DIPRIVAN and generic propofol.

The present inventor has determined that the pain associated with propofol administration can be significantly reduced or eliminated by adjusting the pH of the propofol formulation such that the pH is at least 6.5 at time of administration.

BRIEF SUMMARY OF THE INVENTION

The present invention pertains to pharmaceutical compositions containing propofol and methods of administering a propofol formulation with reduced pain normally associated with propofol administration. The method for propofol administration of the present invention involves administering propofol to the patient at a pH of at least about 6.5. Preferably, the propofol is administered in the form of a pharmaceutical composition containing a pharmaceutically acceptable carrier. If necessary, the pH of the pharmaceutical composition can be adjusted prior to administration to the patient such that the pH is greater than about 6.5. In one embodiment, the propofol is administered to the patient within the pH range of about 6.5 and about 8.5. In another embodiment, the propofol is administered to the patient within the pH range of about 7.1 to about 9.0. In another embodiment, the propofol is administered to the patient within the pH range of about 7.0 to about 8.5. In another embodiment, the propofol is administered to the patient within the pH range of about 7.4 to about 8.0. In another embodiment, the propofol is administered to the patient at a pH greater than about 8.5.

The pharmaceutical composition of the present invention comprises propofol and a pharmaceutically acceptable carrier, wherein the pH of the composition is at least about 6.5. In one embodiment, the pH of the composition is within the pH range of about 6.5 and about 8.5. In another embodiment, the pH of the composition is within the pH range of about 7.1 to about 9.0. In another embodiment, the pH of the composition is within the pH range of about 7.0 to about 8.5. In another embodiment, the pH of the composition is within the pH range of about 7.4 to about 8.0. In another embodiment, the pH of the composition is greater than about 8.5. The pharmaceutical composition can contain alkalizing agents and/or buffering agents to achieve and, preferably, maintain the pH within the desired range.

The pharmaceutical compositions of the present invention are useful as anesthetics, including sedation, and induction and maintenance of general anesthesia. Thus, in another aspect, the present invention provides a method for inducing anesthesia in a patient which comprises administering a composition of the present invention to the patient, thus reducing or eliminating the pain normally associated with propofol administration.

In another aspect, the present invention provides a method for making a pharmaceutical comprising propofol by mixing propofol and a pharmaceutically acceptable carrier and adjusting the pH of the composition such that it has a pH above about 6.5. In one embodiment, the pH of the composition is within the pH range of about 6.5 and about 8.5. In another embodiment, the pH of the composition is adjusted to within the pH range of about 7.1 to about 9.0. In another embodiment, the pH of the composition is adjusted to within the pH range of about 7.0 to about 8.5. In another embodiment, the pH of the composition is adjusted to within the pH range of about 7.4 to about 8.0. In another embodiment, the pH of the composition is adjusted to greater than about 8.5. The pH of the pharmaceutical composition can be adjusted by adding alkalizing agents and/or buffering agents to achieve and, preferably, maintain the pH within the desired range.

In another aspect, the present invention provides an article of manufacture comprising a container containing a liquid pharmaceutical formulation; and a means for determining the pH of the pharmaceutical formulation. Preferably, the liquid pharmaceutical formulation is one that its efficacy and/or physiological acceptability (safety) depends upon its pH. More preferably, the liquid pharmaceutical formulation is one that its efficacy and/or physiological acceptability (safety) depends upon its pH, and the formulation's pH is susceptible drift (upward or downward) under normal storage conditions. In one embodiment, the pharmaceutical formulation comprises propofol.

In another aspect, the present invention provides a syringe preparation comprising a propofol formulation, wherein the propofol formulation comprises propofol and a pharmaceutically acceptable carrier, and wherein the propofol formulation has a pH of about 6.5 or greater.

DETAILED DISCLOSURE OF THE INVENTION

The present invention is based on the discovery that the administration of propofol at an alkalotic pH reduces or eliminates the pain normally associated with propofol administration (e.g., burning and/or stinging sensation). Thus, the method for administering propofol with reduced administration pain comprises administering propofol to the patient at a pH of 6.5 or greater, thereby reducing or eliminating propofol-induced administration pain. The method of the invention can further comprise adjusting the pH of the propofol, as needed, to achieve an alkalotic pH prior to administration to the patient. For example, in one embodiment, the pH is adjusted within 24 hours of administration to the patient. In another embodiment, the pH is adjusted within three hours of administration to the patient. In another embodiment, the pH is adjusted within one hour of administration, and may be adjusted up to immediately prior to administration. When the starting material is at a pH below 6.5, the upward adjustment of the pH is preferably accomplished by the addition of an effective amount of alkalizing agent.

Optionally, the method of the invention further comprises determining the pH of the propofol preparation at least once prior to administration to the patient. The pH determination step can be carried out before, during, and/or after adjusting the pH of the propofol preparation. The pH can be determined by various methods to obtain quantitative or qualitative results. For example, the probe of a pH meter can be contacted with the propofol formulation. Preferably, a standard pH paper test strip is contacted with the propofol formulation and any color change is observed. In another embodiment of the method of the invention, the pH of the propofol preparation is determined at least once during an aforementioned time interval prior to administration, and no pH adjustment is necessary to render it above 6.5.

Without being bound by theory, it is believed that the hydroxyl substituent (—OH) on the benzene ring of propofol (2,6-diisopropylphenol or 2,6-bis(1-methylethyl) -phenol)) becomes dissociated under acidic conditions (e.g., pH less than about 6.5), causing the molecule to become positively charged and stay in the aqueous portion of the solution. Therefore, raising the pH of the solution will move the propofol molecules into the lipid phase of the emulsion and reduce the concentration of free (positively charged) propofol in the aqueous phase of the emulsion. As the injection pain is thought to be related to the concentration of the free propofol in the aqueous phase of the solution, a propofol solution with a pH greater than 6.5 will cause little or no pain upon intravenous injection. The chemical structure of propofol is shown below.

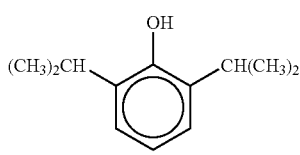

As used herein, the term "alkalizing agent" is intended to mean a compound used to provide alkaline medium for the active agent (propofol). Thus, the pH of the propofol formulation can be increased by adding an amount of alkalizing agent effective to decrease the hydrogen ion concentration of the formulation to a pH of about 6.5 or greater. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids, trolamine, and other known to those of ordinary skill in the art. The alkalizing agent can itself have anesthetic properties, such as thiopental. Alkalizing agents which transiently adjust the pH of the propofol formulation to a desired pH can be utilized, so long as the formulation is administered to the patient while still in the desired pH range (e.g., 6.5 or higher). Preferably, alkalizing agents that stably adjust the pH to a desired level are utilized. Alkalizing agents that also act as buffering agents are preferred.

Optionally, the pharmaceutical composition includes a buffering agent, in addition to the alkalizing agent. Alternatively, the buffering agent can be a substitute for the alkalizing agent, so long as the composition is adjusted to the desired pH range. As used herein, the term "buffering agent" is intended to mean a compound used to resist change in pH upon dilution or addition of acid or alkali. Such compounds include, by way of example, and without limitation, acetic acid, sodium acetate, adipic acid, benzoic acid, sodium benzoate, citric acid, maleic acid, monobasic sodium phosphate, dibasic sodium phosphate, lactic acid, tartaric acid, potassium metaphosphate, potassium phosphate, monobasic sodium acetate, sodium bicarbonate, sodium tartrate, sodium citrate anhydrous and dehydrate, and others known to those of ordinary skill in the art. Inclusion of a buffering agent is preferred for storage of the composition, in order to increase the likelihood that a desired pH is maintained up to the point of administration to the patient. Some agents, such as sodium bicarbonate, are both alkalizing agents and buffering agents, and are preferred.

The pharmaceutical composition of the present invention comprises a pharmacologically effective amount of propofol, or pharmaceutically acceptable salt thereof, and a pharmaceutically acceptable carrier. A "pharmacologically effective amount" refers to that amount of propofol effective to produce the intended pharmacologic result, such as to induce anaesthesia. A "pharmaceutically acceptable carrier" refers to any of the standard pharmaceutical carriers, buffers, and excipients, such as a phosphate buffered saline solution, aqueous solutions of dextrose, and emulsions, such as oil/water or water/oil emulsion, and various types of wetting agents and/or adjuvants.

The pharmaceutical compositions of the subject invention can be formulated according to known methods for preparing pharmaceutically useful compositions. Formulations are described in a number of sources which are well known and readily available to those skilled in the art. For example, Remington's Pharmaceutical Science (Martin E W, Easton Penn., Mack Publishing Company, 19$^{th}$ ed., 1995) describes formulations which can be used in connection with the subject invention, including suitable pharmaceutical carriers. Formulations suitable for parenteral administration include, for example, aqueous sterile injection solutions, which may contain antioxidants, buffers, bacteriostats; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. The propofol used in the compositions and methods of the invention may be in the form of a pharmaceutically acceptable salt. A "pharmaceutically acceptable salt" is a salt that can be formulated into a compound for pharmaceutical use including, e.g., metal salts (sodium, potassium, magnesium, calcium, etc.), and salts of ammonia or organic amines. It should be understood that in addition to the ingredients particularly mentioned above, the formulations of the subject invention can include other agents conventional in the art having regard to the type of formulation in question.

Other components, such as preservatives, stabilizers, coloring preventives, soothing agents, isotonic agents, antibacterial agent, antifungal agent, solubility enhancing agent, complexation enhancing agent, solvent, electrolyte, salt, water, tonicity modifier (e.g., glycerol), antifoaming agent, oil, emulsifying agent, bulking agent, cryoprotectant, and the like, or a combination thereof, may be added as needed. In one embodiment, the composition of the invention does not contain any antibacterial agent or antifungal agent. The composition can contain other anaesthetic agents in admixture, such as lidocaine or sodium thiopental (STP). Preferably, the composition contains an additional anaesthetic that also acts as an alkalizing agent, such as STP. In one embodiment of the composition of the invention, the anaesthetic-alkalizing agent is present in a volumetric ratio between 10:1 propofol:anaesthetic-alkalizing agent and 30:1 propofol:anaesthetic-alkalizing agent, such that a net alkalotic pH is achieved. In another embodiment, the volumetric ratio is in the range of about 18:1 to about 20:1 propofol:anaesthetic-alkalizing agent. It should be understood that the volumetric ratio can be varied, depending upon the alkalinity of the alkalizing agent. In one embodiment, the composition contains no anaesthetic agent other than propofol. Likewise, in one embodiment of the method of the invention, no anesthetic agent other than propofol is administered to the patient.

The present invention also provides a method for making a pharmaceutical composition comprising propofol by mixing propofol and a pharmaceutically acceptable carrier and adjusting the pH of the composition such that it has a pH of 6.5 or greater. In one embodiment, the pH of the composition is within the pH range of about 6.5 and about 8.5. In another embodiment, the pH of the composition is adjusted to within the pH range of about 7.1 to about 9.0. In another embodiment, the pH of the composition is adjusted to within the pH range of about 7.0 to about 8.5. In another embodiment, the pH of the composition is adjusted to within the pH range of about 7.4 to about 8.0. In another embodiment, the pH of the composition is adjusted to greater than about 8.5.

The method of the invention can further incorporate conventional methods for preparation of propofol formulations, such as those disclosed in U.S. Pat. Nos. 4,056,636; 4,452,817; 4,799,846; 5,714,520; 5,908,869; 6,028,108; 6,100,302; 6,140,374; 6,177,477; 6,326,406; and 6,399,087. Typically, propofol, either alone or dissolved in a water-immiscible solvent, is emulsified by means of a surfactant. Suitable surfactants include synthetic non-ionic surfactants, such as ethoxylated ethers and esters and polypropylene-polyethylene block co-polymers, and phosphatides, such as naturally occurring phosphatides, such as egg and soya phosphatides and modified or artificially manipulated phosphatides (for example, prepared by physical fractionation and/or chromatography), or mixtures thereof. Preferred surfactants are egg and soya phosphatides.

According to the methods of the subject invention, propofol can be parenterally administered to a patient, e.g., directly into the bloodstream of a patient (such as intravenously) by bolus injection or by infusion. The propofol can be used for the induction of anaesthesia prior to maintenance with a conventional inhalation anaesthetic, or it may be used as a sole anaesthetic agent of short duration, or by repeated administration or by continuous infusion, it may be used as a sole anaesthetic agent of longer duration. The propofol may also be administered parenterally or otherwise to obtain therapeutic benefits other than, or in addition to, anesthesia.

As used herein, the term "patient" is intended to mean a human or non-human mammal. Thus, veterinary patients, including wild and domesticated animals, such as mice, rats, rabbits, guinea pigs, dogs, cats, pigs, sheep, horses, and cattle are included within the meaning of the term.

Dosage levels appropriate for the induction of the desired degree of anesthesia, for example sedation, or induction of or maintenance of general anesthesia, by the methods and compositions of the present invention will depend on the type of mammal under treatment and the physical characteristics of the particular mammal under consideration. These factors and their relationship in determining this amount are well known to skilled practitioners in the medical arts. Approximate dosage levels may be derived from the substantial literature on propofol, may be tailored to achieve optimal efficiency, and will be contingent on the various factors recognized by those skilled in the medical arts including weight, diet, and concurrent medication. A pharmaceutical composition of the present invention typically comprises 0.1% to 5%, by weight, of propofol. Preferably, the composition comprises from 1% to 2% by weight of propofol. More preferably, the composition comprises about 1% propofol by weight.

According to the present invention, the propofol can be administered to the patient for its anesthetic properties; however, the method of the invention also encompasses administration of propofol to obtain other therapeutic benefits known to be associated with propofol, or yet to be discovered. For example, propofol has been reported to be anti-emetic (Castano et al., *Rev. Esp. Anestesiol. Reanim.*, 42(7):257-260, 1995), an anti-epileptic (Kuisma, M. et al. *Epilepsia*, 36(12): 1241-1243, 1995), an anti-pruitic (Borgeat, A. et al., *Anesthesiology*, 80:642-656, 1994; Lawson, S. et al., *Brit. J. Anesthesia*, 64:59-63, 1990), an antioxidant (U.S. Pat. Nos. 5,308, 874 and 5,461,080; Murphy, P. G., *Br. J. Anaesth.*, 68:613-618, 1992; Aarts, L. et al. *FEBS Let.*, 357(1):83-85, 1995; Cervantes, M. *Arch. Med. Res.*, 26:385-395, 1995), a nitric oxide inducer and vasodilator (Boer, F. et al. *Br. J. Anaesth.*, 65:184-189, 1990; Rovby, J. J. et al. *Anesthesiology*, 75:32-42, 1991; Robinson, B. J. et al. *Anesthesiology*, 86:64-72, 1997), and an inhibitor of lipid peroxidation (Musacchio, E. et al., *Pharmacol. Toxicol.*, 69:75-77, 1991; Eriksson, 0. et al. *Biochem. Pharmacol.*, 44:391-393, 1992). Thus, the pharmacologically effective amount of propofol and its route of administration (e.g., injection, infusion, etc.) will vary with the intended pharmacologic result (e.g., induction of anesthesia, inhibition of convulsions, vasodilation etc.). Regardless of the clinical indication for propofol, the increased pH will reduce or eliminate pain associated with its administration.

In another aspect, the present invention provides an article of manufacture comprising a container containing a liquid pharmaceutical formulation; and a means for determining the pH of the pharmaceutical formulation. Preferably, the liquid pharmaceutical formulation is one that its efficacy and/or physiological acceptability (safety) depends upon its pH. More preferably, the liquid pharmaceutical formulation is one that its efficacy and/or physiological acceptability (safety) depends upon its pH, and the formulation's pH is susceptible drift (upward or downward) under normal storage conditions. In one embodiment, the pharmaceutical formulation comprises propofol. The pH determining means can be, for example, litmus paper or a pH-sensitive colorant wherein a color change provides information concerning the pH of the pharmaceutical formulation. The pH-sensitive colorant can be present within the pharmaceutical formulation or packaged separately from the pharmaceutically formulation and subsequently added. The container can be made by methods and composed of materials known to those of ordinary skill in the art for making pharmaceutical containers. For example, the container may be composed of plastic, glass, or a mixture of such materials. The article of manufacture, optionally, includes packaging material and printed information regarding the containerized pharmaceutical formulation and the means for pH determination.

In another aspect, the present invention provides a syringe preparation comprising a propofol formulation, wherein the propofol formulation comprises propofol and a pharmaceutically acceptable carrier, and wherein the propofol formulation has a pH of about 6.5 or greater. The syringe can be made by methods and composed of materials known to those of ordinary skill in the art for making syringes. For example, the syringe body can be produced by molding a resin using a technique such as injection molding. The resin may comprise a base material such as propylene polymer, with additives such as nucleating agents, neutralizing agents, and antioxidants added to the polymer.

The statement that a composition is "X mM stabilized to a designated pH" means that (1) the pH of the composition is greater than or equal to the designated pH and (2) the addition of up to X millimoles of hydronium ion per liter of the composition does not result in the pH of the composition falling below the designated pH.

As used herein, the term "buffering system" means a composition that comprises either the named acid or base, or any related acid or base. An acid or base is related to a named acid or base if (1) it is a conjugate acid or base of the named acid or base, or (2) its conjugate acid or base is related to the named acid or base. For example, a "carbonate buffering system" includes any composition that comprises carbonate ion, or bicarbonate ion, or carbonic acid. Likewise, a "phosphate buffering system" includes any composition that comprises phosphate ion, hydrogen phosphate ion, dihydrogen phosphate ion, or phosphoric acid.

Unless otherwise noted, pH ranges are inclusive. Ranges delimited by pH values specified to the nearest tenth of a pH unit imply that any pH value that is to be compared to the specified range should likewise be expressed to the nearest tenth. For example, a pH value of 6.96 falls in the range of pH values "between 7.0 and 8.5" because the compared value (6.96) must be expressed to the nearest tenth (7.0) and because the stated range is inclusive by default.

Following is an example which illustrates procedures for practicing the invention. This example should not be construed as limiting. All percentages are by weight and all solvent mixture proportions are by volume unless otherwise noted.

EXAMPLE

Use of Thiopental as Alkalyzing Agent to Reduce Propofol Injection Pain

Adding sodium thiopental (STP) to propofol is a convenient and economic method to reduce propofol injection pain. After approval by the hospital ethics committee, a prospective, double blind study of 139 adults (age 20-60) undergoing general anesthesia (GA) for elective surgery was conducted. No patient was premedicated and each had a 20-gauge intravenous (IV) catheter placed at the dorsum of the hand. Patients were randomly assigned to one of the seven groups, each receiving a predetermined propofol admixture from an unlabeled syringe. Each syringe had a total volume of 20 ml and consisted of 19 or 15 ml of 1% propofol (DIPRIVAN; ASTRAZENECA, Wilmington, Del.) and 1 ml or 5 ml of normal saline (groups NS-1, NS-5), 2.5% STP (STP-1, STP-5), 5% sodium bicarbonate (3 milliequivalents of bicarbonate) (bicarb-1, bicarb-5), or 2% lidocaine (lido-5). Induction of GA was initiated with IV infusion of the admixture at a steady rate of 2 ml/min with a volume dose of 0.1 ml/kg. At 20 seconds after the propofol admixture entered the vein, the patient was asked to report any discomfort or pain, and the response was graded as 0=no pain, 1=mild pain, 2=moderate pain, or 3=severe pain. The induction of GA was continued with the remaining propofol infusion, plus midazolam, fentanyl and atracurium. $X^2$ test was performed to compare the incidence and severity of the injection pain. One-way analysis of variance (ANOVA) was used to compare the demographic and hemodynamic data. P value<0.05 was considered significant.

There was no difference in demographic or hemodynamic data between the groups. The incidence of moderate and severe pain on injection was 50% in NS-1 group and 0% in lido-5 group (both used as control groups). Diluting the propofol alone (NS-5), or adding an inadequate amount of buffer (bicarb-1) was ineffective in reducing the pain (Table 1). However, in groups STP-1, STP-5, and bicarb-5, where pH of the admixture was sufficiently raised to >7.0 (Table 2), the injection pain was effectively blocked (Table 1).

Adding STP, sodium bicarbonate, or other alkalizing or buffering agents to propofol can significantly reduce the pain on injection, due to the increase of pH in the propofol admixture. As a strong basic buffer, as little as 1 ml of STP added to 19 ml of propofol can effectively increase the pH and block the injection pain. Raising the pH of propofol emulsion represents a new alternative to reduce the injection pain.

TABLE 1

Number of patients with different pain scores in each group.

|  | None (0) | Mild (1) | Moderate (2) | Severe (3) | (2) + (3)/ total (%) |
|---|---|---|---|---|---|
| NS-1 | 1 | 8 | 7 | 2 | 9/18 (50%)** |
| STP-1 | 10 | 9 | 2 | 0 | 2/21 (9.5%)* |
| bicarb-1 | 1 | 9 | 10 | 1 | 11/21 (52%)** |
| NS-5 | 2 | 8 | 9 | 2 | 11/21 (52%)** |
| STP-5 | 11 | 8 | 1 | 0 | 1/20 (5%)* |
| bicarb-5 | 8 | 11 | 0 | 0 | 0/19 (0%)* |
| lido-5 | 10 | 9 | 0 | 0 | 0/19 (0%)* |

*p < 0.05 in comparison with NS-1;

**p < 0.05 in comparison with lido-5

TABLE 2

Content and pH value of the propofol admixture in each group.

|  | NS-1 | STP-1 | bicarb-1 | NS-5 | STP-5 | bicarb-5 | lido-5 |
|---|---|---|---|---|---|---|---|
| 20 ml propofol admixture containing | 1 ml NS | 1 ml STP | 1 ml bicarb | 5 ml NS | 5 ml STP | 5 ml bicarb | 5 ml lidocaine |
| pH of the final propofol admixture | 5.5 | 7.7-8.0 | 5.5-6.0 | <5.5 | >10 | 7.0-7.2 | <5.5 | pH values were measured with pH paper strips

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A pharmaceutical composition comprising an oil-in-water emulsion of propofol, wherein the composition comprises about 1% (w/v) propofol, about 10% (w/v) lipid, and, optionally, a pharmaceutically acceptable carrier, wherein a buffering agent is added to the pharmaceutical composition such that the composition can maintain a pH of about 7.1 to 8.5 for at least 6 months and wherein said buffering agent is bicarbonate.

2. A sealed container that contains the pharmaceutical composition of claim 1.

3. The pharmaceutical composition of claim 1, wherein the composition comprises about 100 mg/mL soybean oil.

4. The pharmaceutical composition of claim 1, further comprising glycerol.

5. The pharmaceutical composition of claim 4, wherein the concentration of glycerol is about 22.5 mg/ml.

6. The pharmaceutical composition of claim 1, further comprising egg lecithin.

7. The pharmaceutical composition of claim 6, wherein the concentration of egg lecithin is about 12 mg/ml.

8. The pharmaceutical composition of claim 1, further comprising disodium edentate (EDTA).

9. The pharmaceutical composition of claim 8, wherein the concentration of EDTA is about 0.005% (w/v).

10. The pharmaceutical composition of claim 1, comprising 1.25% sodium bicarbonate.

11. A pharmaceutical composition comprising an oil-in-water emulsion of propofol, wherein the composition comprises 10 mg/mL propofol, 100 mg/mL soybean oil, 22.5 mg/mL glycerol, and 12 mg/mL egg lecithin and, optionally, a pharmaceutically acceptable carrier, wherein a buffering agent is added to the pharmaceutical composition such that the composition can maintain a pH of about 7.1 to 8.5 for at least 6 months and wherein said buffering agent is bicarbonate.

12. The pharmaceutical composition of claim 11, further comprising 0.005% (w/v) EDTA.

13. A sealed container that contains the pharmaceutical composition of claim 11.

\* \* \* \* \*